(12) United States Patent
Liu et al.

(10) Patent No.: US 6,920,398 B2
(45) Date of Patent: Jul. 19, 2005

(54) HAPLOTYPE DETERMINATION (75) Inventors: Jun S. Liu, Weston, MA (US); Zhaohui Steve Qin, Somerville, MA (US); Tianhua Niu, West Roxbury, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 371 days.

(21) Appl. No.: 10/165,946

(22) Filed: Jun. 10, 2002

(65) Prior Publication Data

US 2003/0059808 A1 Mar. 27, 2003

Related U.S. Application Data

(60) Provisional application No. 60/344,443, filed on Nov. 9, 2001, and provisional application No. 60/296,864, filed on Jun. 8, 2001.

(51) Int. Cl.$^7$ ............................................. G06F 19/00
(52) U.S. Cl. ......................................................... 702/20
(58) Field of Search .......................................... 702/20

(56) References Cited

PUBLICATIONS

Altshuler et al., "An SNP map of the human genome generated by reduced representation shotgun sequencing", *Nature* 407:513–516 (2000).
Akey et al., "Haplotypes vs single marker linkage disequilibrium tests: what do we gain?", *Eur J Hum Genet* 9:291–300 (2001).
Beaudet et al., "Homogeneous assays for single–nucleotide polymorphism typing using AlphaScreen", *Genome Res* 11:600–608 (2001).
Bradshaw et al., "A new vector for recombination–based cloning of large DNA fragments from yeast artificial chromosomes", *Nucleic Acids Res* 23:4850–4856 (1995).
Chen and Liu, "Predictive updating methods with application to Bayesian classification", *J. R. Stat. Soc.* B 58:397–415 (1996).
Chiano and Clayton, "Fine genetic mapping using haplotype analysis and the missing data problem", *Ann Hum Genet* 62 (Pt 1):55–60 (1998).
Clark, "Inference of haplotypes from PGR–amplified samples of diploid populations", *Mol Biol Evol* 7:111–122 (1990).
Cox et al., "Data mining: Efficiency of using sequence databases for polymorphism discovery", *Hum Mutat* 17:141–150 (2001).
Daly et al., "High–resolution haplotype structure in the human genome", *Nature Genet* 29:229–232 (2001).
Dempster et al., "Maximum likelihood from incomplete data via EM algorithm", *J Roy Stat Soc* B 39:1–38 (1997).
Douglas et al., "Experimentally–derived haplotypes substantially increase the efficiency of linkage disequilibrium studies", *Nat Genet* 28:361–364 (2001).

Drysdale et al., "Complex promoter and coding region $\beta_2$–adrenergic receptor haplotypes alter receptor expression and predict in vivo responsiveness", *Proc Natl Acad Sci USA* 97:10483–10488 (2000).
Excoffier and Slatkin "Maximum–likelihood estimation of molecular haplotype frequencies in a diploid population", *Mol Biol Evol* 12:921–927 (1995).
Fallin and Schork, "Accuracy of haplotype frequency estimation for biallelic loci, via the expectation–maximization algorithm for unphased diploid genotype data", *Am J Hum Genet* 67:947–959 (2000).
Fallin et al., "Genetic Analysis of Case/Control Data Using Estimated Haplotype Frequencies: Application to APOE Locus Variation and Alzheimer's Disease", *Genome Res* 11:143–151 (2001).
Fan et al., "Parallel genotyping of human SNPs using generic high–density oligonucleotide tag arrays", *Genome Res* 10:853–860 (2000).
Farrall et al., "Fine–mapping of an ancestral recombination breakpoint in *DCP1*", *Nat Genet* 23:270–271 (1999).
Gelman and Speed, "Characterizing a joint probability distribution by conditionals", *J Roy Stat Soc* B 55:185–188 (1993).
Hacia et al., "Determination of ancestral alleles for human single–nucleotide polymorphisms using high–density oligonucleotide arrays", *Nat Genet* 22:164–167 (1999).
Hawley and Kidd, HAPLO: a program using the EM algorithm to estimate the frequencies of multisite haplotypes, *J Hered* 86:409–411 (1995).
Heng and Low, "Cladistic analysis: its applications in association studies of complex diseases", *Ann Acad Med Singapore* 29:313–321 (2000).
Hodge et al., "Loss of information due to ambiguous haplotyping of SNPs", *Nat Genet* 21:360–361 (1999).
Hudson, "Gene genealogies and the coalescent process", *Oxford Surveys in Evolutionary Biology*, vol. 7, Futuyma and Antonovics (eds), Oxford University Press, Oxford, pp 1–44 (1991).

(Continued)

*Primary Examiner*—John S. Brusca
(74) *Attorney, Agent, or Firm*—Fish & Richardson P.C.

(57) ABSTRACT

Haplotypes for phased genotypic information are determined from unphased genotypic information. One exemplary method includes separating a dataset that includes genotypic information for a plurality of markers for each of a plurality of individuals into subdatasets, each subdataset including the genotypic information for a subset of the plurality of markers; for each subdataset, identifying haplotypes compatible with marker information for each marker of the subset and for each individual of the plurality; and for each individual, assembling the haplotypes from each of the subsets to provide the individual's haplotype with respect to the plurality of markers.

27 Claims, 6 Drawing Sheets

PUBLICATIONS http://hjmuller.bio.uci.edu/~labhome/main.html, "What is the Nature of Quantitative Variation?", printed Jun. 6, 2002.

http://hjmuller.bio.uci.edu/~labhome/tools.html, "Tools: Statistical Analysis and Molelcular Biology Tools", printed Jun. 6, 2002.

http://hjmuller.bio.uci.edu/~labhome/coalescent.html, "Using the Coalescent Process to Simulate Gametes from Random Mating Populations with Recombination", printed Jun. 6, 2002.

https:www.fastlane.nsf.gov/servlet/showaward?award=0094613, NSH Award Abstract DMS–0094613: Collaborative Research: Sequential Monte Carlo Methods and Their Applications, printed Jun. 10, 2002, Grant Start Date: Sep. 15, 2000.

Israel et al., "The effect of polymorphisms of the $\beta_2$–adrenergic receptor on the response to regular use of albuterol in asthma", Am J Respir Crit Care Med 162:75–80 (2000).

Judson and Stephens, "Notes from the SNP vs. haplotype front", Pharmacogenomics 2:7–10 (2001).

Kerem et al., "Identification of the cystic fibrosis gene: genetic analysis", Science 245:1073–1080 (1989).

Lander and Botstein, "Homozygosity mapping: a way to map human recessive traits with the DNA of inbred children", Science 236:1567–1570 (1987).

Lawrence et al., "Detecting subtle sequence signals: a Gibbs sampling strategy for multiple alignment", Science 262:208–214 (1993).

Liu, "The collapsed Gibbs sampler Bayesian computation with application to a gene regulation problem", J Am Stat Assoc 89:958–966 (1994).

Liu, "Monte Carlo Strategies in Scientific Computing", Springer–Verlag, New York (Table of Contents only) (2001).

Liu et al., "Bayesian analysis of haplotypes for linkage disequilibrium mapping", Genome Res 11:1716–1724 (2001).

Lizardi et al., "Mutation detection and single–molecule counting using isothermal rolling–circle amplification", Nat Genet 19:225–232 (1998).

Long et al., "An E–M algorithm and testing strategy for multiple–locus haplotypes", Am J Hum Genet 56:799–810 (1995).

Martinez et al., "Association between genetic polymorphisms of the beta2–adrenoceptor and response to albuterol in children with and without a history of wheezing", J Clin Invest 100:3184–3188 (1997).

Michalatos–Beloin et al., "Molecular haplotyping of genetic markers 10 kb apart by allele–specific long–range PCR", Nucleic Acids Res 24:4841–4843 (1996).

Niu et al., "Angiotensin converting enzyme gene insertion/deletion polymorphism and cardiovascular disease: Therapeutic Implications", Drugs 62(7):977–993 (2002).

Nui et al., "Bayesian Haplotype Inference for Multiple Linked Single–Nucleotide Polymorphisms", Am J Hum Genet 70:157–169 (2002).

Niu et al., "Detection of novel ALAD gene polymorphisms using denaturing high–performance liquid chromatography", Hum Biol 73:429–442 (2001).

Pritchard, "Are rare variants responsible for susceptibility to complex diseases?", Am J Hum Genet 69:124–137 (2001).

Ranade et al., "High–throughput genotyping with single nucleotide polymorphisms", Genome Res 11:1262–1268 (2001).

Reich et al., "Linkage disequilibrium in the human genome", Nature 411:199–204 (2001).

Reihsaus et al., "Mutations in the gene encoding for the $\beta_2$–adrenergic receptor in normal and asthmatic subjects", Am J Respir Cell Mol Biol 8:334–339 (1993).

Rieder et al., "Sequence variation in the human angiotensin converting enzyme", Nat Genet 22:59–62 (1999).

Risch, "Searching for genetic determinants in the new millennium", Nature 405:847–856 (2000).

Ross et al., "High–level multiplex genotyping by MALDI–TOF mass spectrometry", Nat Biotechnol 16:1347–1351 (1998).

Rothberg, "Mapping a role for SNPs in drug development", Nature Biotechnology 19:209–211.

Ruano et al., "Haplotype of multiple polymorphisms resolved by enzymatic amplification of single DNA molecules", Proc Natl Acad Sci USA 87:6296–6300 (1990).

Schroeder et al., "Protection against bronchial asthma by CFTRΔF508 mutation: a heterozygote advantage in cystic fibrosis", Nat Med 1:703–705 (1995).

Stephens et al., "A new statistical method for haplotype reconstruction from population data", Am J Hum Genet 68:978–989 (2001).

Templeton, "A cladistic analysis of phenotypic associations with haplotypes inferred from restriction endonuclease mapping or DNA sequencing. V. Analysis of case/control sampling designs: Alzheimer's disease and the apoprotein E locus", Genetics 140:403–409 (1995).

Tishkoff et al., "The accuracy of statistical methods for estimation of haplotype frequencies: an example from the CD4 locus", Am J Hum Genet 67:518–522 (2000).

Toivonen et al., "Data mining applied to linkage disequilibrium mapping", Am J Hum Genet 67:133–145 (2000).

Tyagi and Kramer, "Molecular beacons: probes that fluoresce upon hybridization", Nat Biotechnol. 14:301–308 (1996).

Wallenstein et al., "Logistic regression model for analyzing extended haplotype data", Genet Epidemiol 15:173–181 (1998).

Woolley et al., "Direct haplotyping of kilobase–size DNA using carbon nanotube probes", Nat Biotechnol 18:760–763 (2000).

Zhang et al., "Comparisons of two methods for haplotype reconstruction and haplotype frequency estimation from population data", Am J Hum Genet 69:906–914 (2001).

Zhao et al., "Transmisson/disequilibrium tests using multiple tightly linked markers", Am J Hum Genet 67:936–946 (2000).

Figure 1

$$L = K \times 2^\alpha$$

HAPLOTYPE DETERMINATION

CROSS-REFERENCE TO RELATED APPLICATIONS

This application claims priority to U.S. Application Ser. Nos. 60/296,864, filed on Jun. 8, 2001 and 60/344,443, filed on Nov. 9, 2001, the contents of both of which are hereby incorporated by reference in their entirety for all purposes.

GOVERNMENT SUPPORT

The work described herein was supported in whole or in part by a grant from the United States Government, National Science Foundation, Grant No. DMS-0094613. The United States Government has certain rights in the invention.

BACKGROUND

Single nucleotide polymorphisms (SNPs) are genetic polymorphisms which can be found every 250–350 base pairs in the human genome (Beaudet et al. 2001). SNPs are useful, for example, for mapping the genetic components of complex diseases and drug responses. Because SNPs are typically biallelic, SNP genotyping is more amenable to automation and miniaturization than microsatellite loci. SNP genotyping can use a variety of high-throughput genotyping platforms, such as mass spectrometry (Ross et al. 1998), molecular beacons (Tyagi and Kramer 1996), TaqMan™ assay (Ranade et al. 2001), and high-density oligonucleotide microchips (Hacia et al. 1999), as well as other methods such as denaturing high performance liquid chromatography and fluorescence-based DNA sequencing (Niu et al. 2001a) or in silico SNP screening (Cox et al. 2001).

A variety of genotyping techniques, including many implementations of the above examples, are available to determine for a given locus, whether or not an individual has a particular allele. Frequently, the genotyping techniques only provide unphased genetic information. In other words, the methods can indicate whether a particular allele is present in an individual at a given locus, but not whether it is on the same chromosome as other alleles. In contrast, phased genotypic information includes information about whether a particular allele is on the same chromosome as an allele of another locus. Resolving an individual's haplotype (in other words, "phasing" the genotypic information) requires determining or inferring whether an allele is present on the maternal chromosome, paternal chromosome, both chromosomes, or neither. Haplotypic information includes the results of such a determination for multiple linked alleles.

In the following example, the presence of a particular allele of a biallelic marker is indicated by a "1"; its absence is indicated by a "0." There is usually more than one possible solution to the phasing problem, as is evident for the following example which considers five linked genetic biallelic loci:

| UNPHASED: | 1 1 0 1 0 |
| MATERNAL: | 1 1 0 1 0 |
| PATERNAL: | 1 0 0 0 0 |

Absent other information, alternate solutions are possible. One alternate solution is:

| UNPHASED: | 1 1 0 1 0 |
| MATERNAL: | 0 1 0 1 0 |
| PATERNAL: | 1 1 0 0 0 |

However, the tremendous amount of SNP data presents a challenge for haplotype determination. The challenge arises in part because (1) a single SNP has a relatively low information content, and (2) for a gene with multiple tightly linked SNPs, not only would the locus disequilibrium (LD) information contained in flanking markers be ignored in the single SNP-based approach, but also a Bonferroni correction is often required to protect against an inflated type I error. Thus, the "haplotype-centric" approach, which combines the information of adjacent SNPs into composite multi-locus haplotypes, is more desirable. Haplotypes not only are more informative, but also capture the regional LD information, which is arguably more robust and powerfull (Pritchard 2001; Akey et al. 2001; Daly et al. 2001).

For autosomal loci, if only the multilocus phenotypes ("phenotype," in this context, denotes unphased genotype configurations) for each individual are provided, the phase information for those individuals with multiply heterozygous phenotypes is inherently ambiguous. Whenever a particular individual has no more than one heterozygous site, the situation is simple and the individual's haplotype phase can be resolved with certainty. True resolution for the ambiguous (i.e., multiply heterozygous) phenotypes depends on molecular haplotyping or typing of close biological relatives. For molecular haplotyping, existing methods include: single molecule dilution (Ruano et al. 1990), allele-specific long-range PCR (Michalatos-Beloin et al. 1996), isothermal rolling circle amplification (Lizardi et al. 1998), long-insert cloning (Bradshaw et al. 1995; Ruano et al. 1990), and carbon nanotube probing (Woolley et al. 2000), and the diploid-to-haploid conversion method (Douglas et al. 2001). See also (Judson and Stephens 2001) for a discussion.

The typing of close relatives can reduce the phase ambiguity, but the phase determination can still be problematic when the number of loci is only moderately large (Hodge et al. 1999).

Existing in silico haplotype determination methods can be use to phase commonly-occurring haplotypes in a reasonably-sized sample of individuals even when some of the model assumptions are strongly violated. There are primarily three categories of algorithms for inferring haplotype phases of individual genotype data: Clark's algorithm (Clark 1990), the expectation-maximization (EM) algorithm (Excoffier and Slatkin 1995; Chiano and Clayton 1998; Hawley and Kidd 1995; Long et al. 1995), and a pseudo-Bayesian algorithm (Stephens et al. 2001a).

Clark's parsimony approach attempts to assign the smallest number of haplotypes for the observed genotype data through convoluted updating of the haplotype list starting from phase-unambiguous individuals. Clark's algorithm has been used to delineate gene-based haplotype variations (Stephens et al. 2001b) and the genome-wide LD in populations with different histories (Reich et al. 2001).

The EM algorithm starts with an initial guess of haplotype frequencies and iteratively updates the frequency estimates so as to maximize the log-likelihood function. An EM-based haplotype estimation has been used in the transmission disequilibrium tests (Zhao et al. 2000), and can function under a wide range of parameter settings (Fallin and Schork 2001).

Stephens et al. (2001a) employed an iterative stochastic sampling strategy (the Pseudo-Gibbs Sampler, or PGS henceforth) for the assignment of haplotype phases. The performance of the PGS is likely due to both the employment of a stochastic search strategy and the incorporation of the coalescence theory in its iteration steps. The coalescence model is appropriate, for example, for describing a stable population that has evolved for a long period of time.

SUMMARY OF THE INVENTION

The inventors have discovered, in part, methods of determining an individual's haplotype from marker information for a group of individuals. The methods allow for deconvolution or phasing of marker information into haplotype information for each chromosome.

In one aspect, the invention features the so-called partition-ligation method. The method includes: separating a dataset that includes genotypic information (e.g., unphased genotypic information) for a plurality of markers for each of a plurality of individuals into subdatasets, each subdataset including the genotypic information for a subset of the plurality of markers; for each subdataset, identifying haplotypes compatible with marker information for each marker of the subset and for each individual of the plurality; and for each individual, assembling the haplotypes from each of the subsets.

The method can be repeated, e.g., to stepwise assemble haplotypes from multiple subsets. For example, the dataset is separated into a number of subsets, the number being a power of two ($2^x$). In each cycle, two adjacent subsets are assembled. After x cycles, the complete haplotypes are assembled.

An algorithm can be used to identify haplotypes for each subset. For example, the algorithm can maximize the likelihood of haplotype frequencies in a population, e.g., assuming a Hardy-Weinberg equilibrium. Examples of such an algorithm include Gibbs sampling methods and the Expectation-Maximization (EM) algorithm (e.g., as described by Excoffier and Slatkin, *Mol. Biol. Evol.* 12, 921–927 (1995)). The algorithm can use a Markov chain Monte Carlo algorithm. In another example, the algorithm includes a parsimony method.

In some embodiments, the subsets are adjacent and non-overlapping. In other embodiment, the subsets are overlapping. In still other embodiments, at least one of the subsets is interleaved, and either non-overlapping or overlapping. By "overlapping," it is meant that two subsets include common elements. By "interleaved," it is meant that, when aligned in linear order with respect to a chromosome, at least one marker from one set is present between the terminal markers for another set.

The dataset can include missing or ambiguous marker information. The dataset can include marker information for at least 12, 20, 40, 50, 100, 500, 1000, or 10000 individuals. The dataset can include marker information for at least 2, 3, 4, 6, 8, 10, 15, 20, 40, 50, 100, 200, 400 or more markers. The markers can be SNPs, RFLPs, repeats, and so forth. The dataset can be for any diploid or polyploid organism, e.g., a mammal (humans, domesticated animals, endangered animals, and so forth), a plant, an insect, or a model organism for experimentation (e.g., *C. elegans, Drosophila,* or *Danio rerio*).

In some embodiments, the method assigns an allele to a marker that is ambiguous or unknown.

The method can be a machine-based method, or can be implemented otherwise, e.g., manually. The method can further including, e.g., prior to the separating, providing a nucleic acid sample from one or a plurality of subjects and analyzing the sample(s) to determine genotypic information for each marker of the plurality for the subject. Exemplary methods for genotyping include the oligonucleotide ligation assay, single-base extension assays, and DNA chip hybridization.

The method can also include outputting the one or more of the assembled haplotypes, e.g., displaying information about the assembled haplotypes on a console, printing information about the assembled haplotypes, or communicating information about the assembled haplotypes, e.g., electronically, e.g., by email.

In another aspect, the invention features the so-called prior-annealing method. The method includes: providing an initial probability distribution for a set of haplotypes; selecting (e.g., at random or iteratively) an individual from a plurality of individuals; identifying haplotypes compatible with marker information for the selected individual, based on the initial probability distribution; updating the probability distribution; and iterating the method, e.g., to converge on a solution of haplotypes for each individual of the plurality.

The initial probability distribution function can have a very high pseudo-count for the prior Dirichlet distribution of the haplotype frequencies. Each iteration can reduce the number of pseudo-counts.

The method can further include a local updating routine.

The dataset can include missing or ambiguous marker information. The dataset can include marker information for at least 12, 20, 40, 50, 100, 500, 1000, or 10000 individuals. The dataset can include marker information for at least 2, 3, 4, 6, 8, 10, 15, 20, 40, 50, 100, 200, 400 or more markers. The markers can be SNPs, RFLPs, repeats, and so forth. The dataset can be for any diploid or polyploid organism, e.g., a mammal (humans, domesticated animals, endangered animals, and so forth), a plant, an insect, a model organisms for experimentation (e.g., *C. elegans, Drosophila,* or *Danio rerio*).

The prior-annealing method can be used in combination with the partition-ligation method. The method can also include other features described herein.

In yet another aspect, the invention features a method for determining haplotypes of a plurality of individuals from marker information. The method includes providing an frequency table for haplotypes (e.g., all possible haplotypes); selecting an individual (e.g., iteratively or randomly) from the plurality of individuals; and drawing a compatible haplotype by sampling haplotypes based a joint distribution function. The joint distribution function can be processed by integrating out the frequency table. The method can be repeated, e.g., until a solution is converged upon. See, also the predictive updating strategy, described herein.

In another aspect, the invention features a method that includes: a method comprising: sending, to a computer unit, unphased genotypic information about a plurality of gene markers for a plurality of individuals; and receiving, from the computer unit, phased genotypic information about the plurality of gene markers for the individual, wherein the computer unit determined the phased genotypic information using a method described herein.

The method can further including, e.g., prior to the sending, providing a nucleic acid sample from one or a plurality of subjects and analyzing the sample(s) to determine genotypic information for each marker of the plurality for the subject. Exemplary methods for genotyping include the oligonucleotide ligation assay, single-base extension assays, and DNA chip hybridization.

The method can also include outputting at least some of the received phased genotypic information, e.g., displaying information about the assembled haplotypes on a console, printing information about the assembled haplotypes, or communicating information about the assembled haplotypes, e.g., electronically, e.g., by email.

In another aspect, the invention features an article that includes a machine-readable medium that stores machine-executable instructions. The instructions cause a machine to process marker information for a plurality of individuals using the partition-ligation method, the prior-annealing method, the predictive-updating strategy, or a combination thereof.

In still another aspect, the invention features a system that includes a processor and a memory store. The system can also include a user-interface, e.g., for displaying output and/or for accepting user-defined parameters. The processor is configured to process marker information for a plurality of individuals using a method described herein, e.g., the partition-ligation method, the prior-annealing method, the predictive-updating strategy, or a combination thereof. The memory store is capable of storing marker information for the plurality of individuals and/or haplotype information for the plurality of individuals.

The invention also features a database that includes a first table of records, each record including allelic information for a plurality of markers on a chromosome, and a measure of uncertainty for each marker. The measure of uncertainty can be a function of the probability distribution of haplotypes. The database can also include a second table of records that stores frequency information for a collection of haplotypes. The database can also include a third table of records that includes parameters for a probability function.

The database can be store in machine-readable form, e.g., in a computer memory store or on computer-readable media.

As used herein "determining" haplotypes or phased genotypic information includes methods that use inference, e.g., from statistical information. Of course, true resolution of a haplotype may require molecular analysis of genetic material.

Abbreviations: PCR=Polymerase Chain Reaction; SNP=single nucleotide polymorphism; RFLP=restriction fragment length polymorphism; EM=Expectation-Maximization; PGS=Pseudo Gibbs Sampler; HWE=Hardy Weinberg Equilibrium; MC=Monte Carlo; MLE=maximum likelihood estimate; PL=partition-ligation; ACE=angiotensin I converting enzyme; CFTR=cystic fibrosis transmembrane conductance regulator.

All patents, and references, including Niu et al. (2002) *Am. J. Hum. Genet.* 70:157–169, are incorporated by reference in their entirety for all purposes.

DESCRIPTION OF THE DRAWINGS

FIG. 2. The impact of Hardy-Weinberg Equilibrium (HWE) violation on the performances the PL, PGS, Clark's, and EM algorithms. The simulation study was conducted under five scenarios, each with 1,000 replications: 1) neutral; 2) moderate heterozygosity; 3) strong heterozygosity; 4) moderate homozygosity; and 5) strong homozygosity. For each trial, a chi-square test statistic for testing the HWE (after pooling the categories with small counts, this gives rise to the independence test of a 4×4 table, which has 9 degrees of freedom) was computed, the number of homozygotes counted, and the error rates of each algorithm recorded. Some results are shown here: (A) The average error rate (defined as the number of erroneous phase calls divided by the total number of phase calls) of each method vs. the HWE chi-square test statistic after combining the simulations from models 1), 2) and 3). (B) The average error rate vs. HWE chi-square test statistic after combining the simulations from models 1), 4) and 5). Note that the chi-square values of 21.67, 16.92, and 14.68 correspond to the $99^{th}$, $95^{th}$, and $90^{th}$ percentiles, respectively. (C) The average error rate vs. sample haplotype homozygosity after combining all the simulations. (D) The zoom-in view of (C) at the left tail of the homozygosity distribution (i.e., 0/15–3/15).

DETAILED DESCRIPTION

Haplotypes have gained increasing attention in complex disease gene mapping because of the abundance of single nucleotide polymorphisms (SNPs) and the limited power of the conventional single-locus analyses. The following description provides, among other things, an exemplary Monte Carlo method for determining haplotypes. The method can include partitioning input information into smaller segments and then constructing partial haplotypes of each segment and to assemble all the segments together. The Gibbs sample, for example, can be used for constructing the partial haplotypes.

In particular, we first partition the whole haplotype into smaller segments. Then, we use the Gibbs sampler both to construct the partial haplotypes of each segment and to assemble all the segments together. Our algorithm can infer haplotypes accurately and rapidly for a large number of linked SNPs. By using a wide variety of real and simulated datasets, we demonstrate the advantages of our Bayesian algorithm, and we show that it is robust to the violation of Hardy-Weinberg equilibrium, the presence of missing data, and occurrences of recombination hotspots.

Several challenges for the haplotype inference include: handling different types of missing marker data (see Methods for details) and handling of a very large number of linked SNPs. Here, we introduce a robust Bayesian procedure that makes use of the same statistical model as that in the EM algorithm and imposes no assumptions on the population evolutionary history. In this model, each individual's haplotype pair is treated as two random draws from a pool of haplotypes with unknown population frequencies. By employing two techniques, partition-ligation and prior annealing, which improve both the accuracy and capacity, our new method showed improved performances in comparison with existing methods in a wide variety of simulated and real datasets. We demonstrate that both the EM and our method performed robustly, including when the Hardy-Weinberg equilibrium (HWE) assumption is violated.

Methods

Statistical Model and Maximum Likelihood Estimation

Consider a sample of n individuals for a local chromosomal region comprising L linked SNPs. Let $Y=(y_1, \ldots, y_n)$ denote the observed genotype for the n individuals, where $y_i=(y_{i1}, \ldots, y_{iL})$, and $y_{ij}$ denote the genotype for individual i at locus j. Let $y_{ij}=0$, 1, or 2 denote that individual i being heterozygous, homozygous wild type, or homozygous mutant at SNP marker locus j, respectively. Additional categories are created for two missing alleles (3) and the presence of only one missing allele, when the known allele is either wild type (4) or mutant (5).

Let $Z=(z_1, \ldots, z_n)$ denote the unobserved haplotype configuration compatible with Y, where $z_i=(z_{i1}, z_{i2})$ designates the assigned haplotype pair for the ith individual. We use the notation $z_{i1} \oplus z_{i2}=y_i$ to denote that the two haplotypes are compatible with genotype $y_i$. Let $\Theta=(\theta_1, \ldots, \theta_M)$ denote population haplotype frequencies, where M is the number of all possible haplotypes. Suppose the HWE holds true, i.e., the population fraction of individuals with the ordered haplotype pairs (g, h) is $\theta_g \theta_h$. Then, the likelihood function can be written out easily as $$P(Y \mid \Theta) = \prod_{i=1}^{n} P(y_i \mid \Theta) = \prod_{i=1}^{n} \sum_{(g,h): g \oplus h = y_i} \theta_g \theta_h.$$

By simple algebra, we can show that the maximum likelihood estimate (MLE) of $\Theta$ has to satisfy the estimating equation:

$$\theta_g = \frac{E_\Theta(n_g \mid Y)}{2n},$$

where $n_g$ is the count of haplotype g in a particular phase configuration Z. Thus, the right-hand-side of the equation computes the "expected frequency" of haplotype g by averaging over all compatible Z's. This equation represents the internal consistency of the MLE and gives rise to the following iteration steps for the EM algorithm (Dempster et al. 1977):

$$\theta_g^{(t+1)} = E_{\Theta^{(t)}}(n_g \mid Y)/2n \tag{1}$$

where $\Theta^{(t)}$ and $\theta_g^{(t+1)}$ refer to the estimated frequencies at time t and t+1, respectively. A formal EM algorithm iterates (1) until $\Theta^{(t)}$ does not change much. Individuals' genotypes can be phased by using the final estimate $\hat{\Theta}$. That is, for a given $y_i$, one finds a compatible haplotype pair (g, h) that maximizes $\hat{\theta}_g \hat{\theta}_h$. One can also impute multiple haplotype pairs so as to reflect the estimation uncertainty.

Bayesian Inference and Gibbs Sampling

Instead of the MLE approach, one can also seek a Bayesian solution to the problem. Assuming that $\Theta \sim$ Dirichlet $(\beta)$ a priori, where $\beta=(\beta_1, \ldots, \beta_M)$ (see Appendix), we have $$P(Y, Z, \Theta) \propto \left(\prod_{i=1}^{n} \theta_{z_{i1}} \theta_{z_{i2}}\right) \left(\prod_{g=1}^{M} \theta_g^{\beta_g - 1}\right)$$

for Z compatible with Y; and $P(Y, Z, \Theta)=0$ otherwise. The following iterations constitute a Gibbs sampling algorithm:

Conditional on $\Theta$, sample a pair of compatible haplotypes for each subject according to $$P(z_i = (g, h) \mid \Theta, y_i) = \frac{\theta_g \theta_h}{\sum_{g' \oplus h' = y_i} \theta_{g'} \theta_{h'}}.$$

Conditional on the "imputed" haplotypes Z, update $\Theta$ by a random draw from the posterior distribution $$P(\Theta \mid Y, Z) = \text{Dirichlet}(\beta + N(Z)),$$

where $N(Z)$ is the vector of haplotype counts in Z.

Predictive Updating

The predictive updating strategy (Liu 1994; Chen and Liu 1996) can be applied to further improve the above Gibbs sampling method. That is, one can integrate out $\Theta$ explicitly in the joint distribution $P(Y, Z, \Theta)$ so that $$P(Y, Z) \propto \frac{\Gamma(|\beta + N(Z)|)}{\Gamma(\beta + N(Z))} \tag{2}$$

where we define $\Gamma(|v|) = \Gamma(|v_1 + \ldots + v_k|)$ and $$\Gamma(v) = \prod_{j=1}^{k} \Gamma(v_j)$$

for a vector $v=(v_1, \ldots, v_k)$. As a consequence, we obtain a different Gibbs sampler: Pick an individual i at random (or in a certain order) and update his/her haplotype $z_i$ by sampling from $$P(z_i=(g, h) \mid Z_{[-i]}, Y) \propto (n_g + \beta_g)(n_h + \beta_h),$$

where $Z_{[-i]}$ represents all but the ith person's haplotypes, $n_g$ and $n_h$ are the counts of haplotypes g and h in $Z_{[-i]}$, respectively. This strategy gives rise to an intuitive algorithm that is similar in spirit to the Gibbs motif sampler for sequence analysis (Lawrence et al. 1993). Stephens et al.

(2001a) also made use of this simple structure in the construction of their PGS algorithm.

Partition-Ligation

Handling a large number of haplotypes is challenging for the Gibbs samplers just described. Here we tackle the problem by a divide-conquer-combine technique named partition-ligation (PL). This technique not only allows us to analyze very long SNP sequences but also helps the Monte Carlo algorithm converge more rapidly. In contrast to a Gibbs sampler that deals with the problem by local updating, i.e., updating a few loci of a person conditional on others (Stephens et al. 2001a), the PL strategy is more similar in spirit to multi-grid Monte Carlo and sequential Monte Carlo (Liu 2001). Suppose a sequence consists of L SNP loci. Without loss of generality, we assume that L=K×M, where K represents the size of each "atomistic unit" (we typically chose $K \leq 8$). The genotype data Y and haplotype data Z are first partitioned into M subsets of size K each (FIG. 1), i.e., $$Y=(Y_{[1:K]}, Y_{[K+1:2K]}, \ldots) \text{ and } Z=(Z_{[1:K]}, Z_{[K+1:2K]}, \ldots)$$

Two strategies can be employed for the ligation step: progressive ligation, and hierarchical ligation. In both approaches we conduct first the atomistic haplotype restoration, i.e., the construction of a set of partial haplotypes implied by each atomistic unit. For example, we process all the possible haplotypes implicated by the first genotype segment $Y_{[1:K]}$. Since the number of loci is moderate (typically, $K \leq 8$), we can implement the aforementioned Gibbs samplers. Then, we record the B most probable haplotypes, $\{z_{[1:K]}^{(1)}, \ldots, z_{[1:K]}^{(B)}\}$, that guarantees that $Y_{[1:K]}$ can be completely "resolved," together with their estimated population frequencies. By the same token, other atomistic units, $Y_{[aK+1:aK+K]}$, can be processed to obtain their most probable haplotypes $\{z_{[aK+1:aK+K]}^{(1)}, \ldots, z_{[aK+1:aK+K]}^{(B)}\}$. The choice of B (between 40 and 50 in all of our examples) depends on both the sample size and heterozygosity of the dataset. It is important to keep B moderately large so as not to discard some haplotype segments that lead to the true haplotypes.

In progressive ligation, we combine the first two atomistic units to form B most probable partial haplotypes of 2K loci, $\{z_{[1:2K]}^{(1)}, \ldots, z_{[1:2K]}^{(B)}\}$, with their estimated frequencies. More precisely, we conduct the Gibbs iterations based on (2) using only the segments of haplotypes, i.e., each person's haplotypes are chosen among the $B^2$ possible combinations of $(z_{[1:K]}^{(i)}, z_{[K+1:2K]}^{(j)})$. This process is continued recursively by ligating the next atomistic unit to the current partial haplotype until all the units are ligated to form the whole haplotype.

Figure 1:
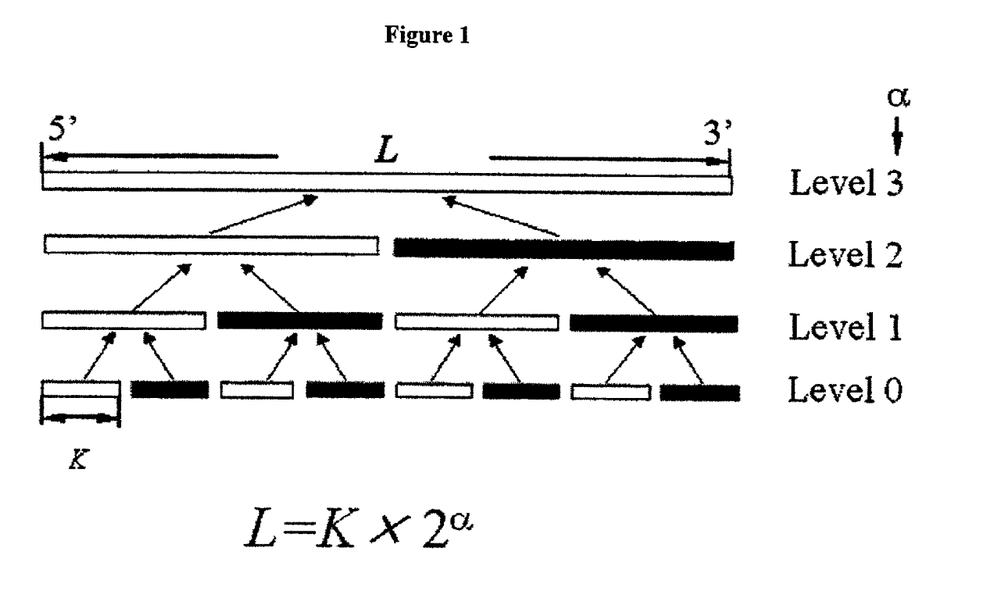
FIG. 1. A schematic diagram depicting the partition-ligation algorithm. L denotes the total number of loci; K denotes the number of loci in the smallest segment; α is the highest level of the partition-ligation pyramidal hierarchy.

For an easy description, we assume that $L=K \times 2^\alpha$ in hierarchical ligation (it can be easily modified to suit for other type of L). Similar to progressive ligation, we have $2^\alpha$ atomistic units, each containing K loci. Then, as shown in FIG. 1, the (2j−1)th segment is ligated with the (2j)th segment for $j=1, \ldots, 2^{\alpha-1}$ to form $2^{\alpha-1}$ level-1 "larger" segments. Then we ligate the adjacent level-1 segments to form $2^{\alpha-2}$ level-2 segments, and so on. The ligation procedure is the same as that described above.

For a dataset with n individuals and L linked SNPs, the running time of the PL algorithm is O(nL), provided that K, B, and the numbers of the Gibbs iterations per individual for both the atomistic haplotype construction and the ligation steps remain constant. This is because that the hierarchical ligation can be represented by a binary tree of depth $[\log_2 L]-1$ with $[L/K]$ leafs. Hence, the PL needs $[L/K]$ atomistic restorations and $[L/K]-1$ ligations per individual.

Prior Annealing

To enable the Gibbs sampler to maneuver in the haplotype space freely, we applied the prior annealing technique: in the beginning of the iteration, high pseudo-counts, $\beta^{(0)}$, that conform to the Dirichlet distribution, are used as the initial prior. As the iteration proceeds, the pseudo-counts are dwindled in a fixed rate. To be specific, suppose the pseudo-counts for all haplotypes are $\beta^{(0)}$ and $\beta^{(T)}$ for the start and the end of Tth iteration, then the pseudo-counts at the tth iteration, $\beta^{(t)}$, is given as the following:

$$\beta^{(t)} = \beta^{(0)} + t(\beta^{(T)} - \beta^{(0)})/T.$$

Missing Marker Data

The problem of missing both alleles of a SNP marker is common due to PCR dropouts and was first addressed by Hawley and Kidd (1995). However, the "one-allele" missing problem, in which only one allele for a particular SNP is unscored due to ambiguity, is also a legitimate concern for a number of SNP genotyping methodologies such as oligonucleotide ligation assay or single base extension (SBE) coupled with fluorescence polarization detection. For example, the new high-throughput SNP genotyping technique TAG-SBE method (Fan et al., 2000), which analyzes allele-specific SBE reactions on standardized high-density oligonucleotide arrays, has a number of advantages such as parallelism, flexibility, and robustness. However, at least in some implementations, in about 1% genotype calls for heterozygous sites it can only score one allele unequivocally. In our algorithm, the missing data are classified into three categories: type I for both alleles missing; type II for one known wild type allele; and type III for one known mutant allele. All the missing types can be handled by the PL with small modifications in its sampling steps: For type I, all the different alleles at the locus are considered without constraint; for types II and III, the sampling choices are partially constrained due to the presence of the known allele.

Implementation of the Algorithms

We implemented Clark's and the PGS algorithms using existing software packages. HAPINFERX, which implements Clark's algorithm, was kindly provided by A. G. Clark. PHASE, which implements the PGS algorithm as described in Stephens et al. (2001a), was downloaded from their website. The EM algorithm for haplotype construction was coded by ourselves (named EM-DeCODER) according to formula (1). The PL idea can also be applied to the EM algorithm with minor modifications. Our simulations suggest that the PL idea serves not only as an effective computational trick, but also as a "regularizer" to prevent the algorithm from being too "greedy." Our Gibbs sampler with the PL and prior annealing procedures is generally referred to as "the PL algorithm," and was coded in a software package named HAPLOTYPER.

Results

To illustrate our algorithm and to compare with existing ones, we analyzed two real datasets and conducted several simulation studies. A distinguishing feature of some of our simulation studies is the use of recently published real haplotypes, e.g., the $\beta_2$-adrenergic receptor gene, the angiotensin I converting enzyme gene, the cystic fibrosis transmembrane conductance regulator gene, and the 5q31 region. We have also conducted two population theory-based simulations, one of which follows the coalescence model and the other produces artificial populations that experienced a "bottle-neck" effect.

$\beta_2$-Adrenergic Receptor ($\beta_2$AR) Gene Dataset

The gene encoding $\beta$2AR is devoid of introns within its coding region. Abnormality of the $\beta$2AR has been hypothesized to be involved in the physiology of asthma (Reihsaus et al. 1993). Because the albuterol, the effective bronchodilator used as a first-line drug for treatment of asthma act primarily by binding to $\beta$2AR expressed on the airway smooth muscle cells, several studies suggest that molecular variants of this gene may predict patients' response to $\beta$2-agonist (Drysdale et al. 2000; Israel et al. 2000; Martinez et al. 1997). According to the data presented in Drysdale et al. (2000), 10 distinct haplotypes, each with L=13 loci, were found in a population of 121 Caucasian subjects. The chi-square test for the data indicates that the HWE holds well (p=0.32). The EM, PGS and the PL algorithms phased all the 121 individuals successfully, whereas Clark's algorithm made two mistakes (i.e., predicted 2 individuals' phases incorrectly).

Impact of the HWE Assumption

In order to assess the sensitivity of the algorithms to the HWE assumption, we took the 12 haplotypes together with their observed frequencies from the $\beta$2AR dataset and carried out simulations using five different models to represent different levels of departures from the HWE. For each model, 1,000 replications were conducted. In each replication, the genotypes of 15 hypothetical individuals were drawn independently from the space of all ordered pairs of haplotypes according to a probability matrix C= $(c_{ij})_{12\times12}$ (i.e., $c_{ij} \geq 0$, and $\Sigma c_{ij}=1$). That is, one has probability $c_{ij}$ to pick haplotype pair $(h_i, h_j)$. The matrix C followed distribution Dirichlet(100D) (see Appendix), where D= $(d_{ij})_{12\times12}$ is also a probability matrix, satisfying the relationship $D \propto P^T W P$ with $P=(p_1, \ldots, p_{12})$ being the vector of the observed frequencies of the 12 haplotypes. Because $d_{ij}= w_{ij}p_ip_j$, letting $w_{ij}=1$ tends to produce samples conforming to the HWE. Matrix W can be interpreted as the fitness of individuals with that particular genotypes and can be controlled to reflect the degree of departure from the HWE. For simplicity, we let $$W = \begin{pmatrix} a & b & \cdots & b \\ b & a & \cdots & \vdots \\ \vdots & \vdots & \ddots & b \\ b & \cdots & b & a \end{pmatrix}.$$

Hence, a>b implies that the homozygous state is preferred and vice versa. The five models are: (1) neutral: a=b=1; (2) moderate heterozygote favoring: a=1, b=2; (3) strong heterozygote favoring: a=1, b=3; (4) moderate homozygote favoring: a=2, b=1; and (5) strong homozygote favoring: a=3, b=1. For each of the five models, the instances of incorrectly inferred haplotype phases, the values of a chi-square statistic (with 9 d.f.) that tests for the HWE, and the number of homozygotes among the 15 individuals are recorded.

Figure 2:
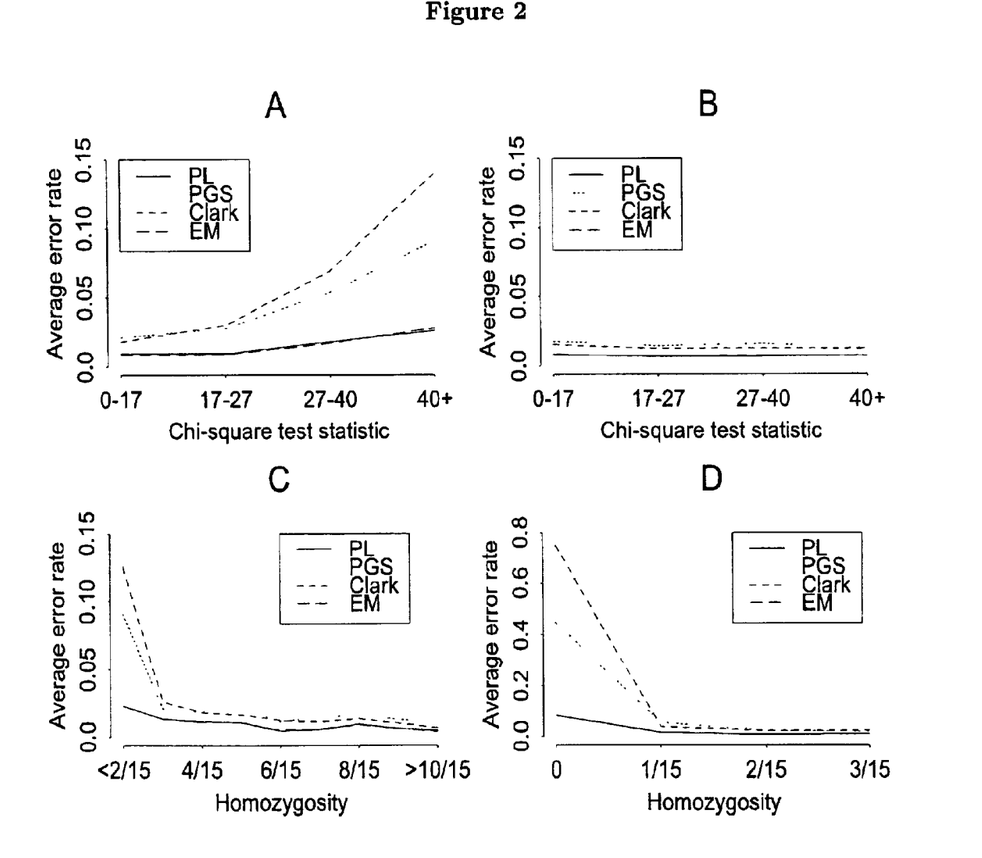

The impact of HWE violation on the PL, Clark's, EM and PGS algorithms are demonstrated in FIG. 2, based on which we made the following observations: (1) A greater extent of the HWE violation due to an excess of heterozygosity leads to a higher error rate for all the four algorithms. (2) In this instance, Clark's and PGS algorithms performed worse across the board and were more vulnerable to the departure from HWE than the EM and PL algorithms; the PL and EM algorithms performed indistinguishably in all the cases. (3) The level of homozygosity correlates more directly with the inference accuracy than the chi-square test statistic (details shown below).

The same extent of the HWE violation according to the chi-square test can be caused by either a significant excess of homozygosity due to inbreeding (Lander and Botstein 1987) or a significant excess of heterozygosity due to its selective advantage (Schroeder et al. 1995). When the former is true, we observed that the algorithms' accuracies were not compromised by the HWE violation (FIG. 2B); whereas when the latter is the case, the number of phasing errors increased monotonically along with the test statistic (FIG. 2A). Thus, the chi-square test statistic alone confounds two distinct scenarios and is not a good indicator of the "difficulty level" of the dataset. In contrast, when the error rates of the phase prediction were stratified according to the number of homozygotes present in the sample, the performances of each algorithm in the 5 simulation models were similar; implying that the sample homozygosity is a good indicator for the difficulty level of the dataset for all the algorithms. FIGS. 2C and 2D display the pooled results from all simulations.

It is worthwhile to emphasize that although the PL and EM methods make an explicit assumption of the HWE, these two methods were in fact much less affected by strong departures from the HWE than either Clark's or the PGS algorithms, neither of which made an explicit HWE assumption. Clark's algorithm under-performed other methods in the case when too few homozygotes are present in the population, but its performance improved more rapidly than the others with the increase of homozygotes in the sample, and it outperformed the PGS when there were a significant proportion of homozygous individuals.

Angiotensin I Converting Enzyme (ACE) Gene Dataset

The ACE gene is an intriguing candidate in pharmacogenetic studies of the widely used ACE inhibitors for treatment of essential hypertension and congestive heart failure (Niu et al. 2001b). The human ACE gene contains 26 exons, with exons 4–11 and 17–24 encoding two homologous domains of the ACE molecule are highly similar both in size and in sequence indicating the occurrence of a gene duplication event during the evolutionary process. Rieder et al. (1999) completed the genomic sequencing of ACE gene for 11 subjects. A total of 78 varying sites in 22 chromosomes were identified over a genomic region of >15 kb, and data on 52 biallelic-markers are available (Rieder et al. 1999).

In order to test the stability of the algorithms, we performed 100 runs for each algorithm and presented them in table 1. Since the EM algorithm is limited in the number of heterozygous loci allowable in the genotype data (the upper limit is ~15 segregating loci), it was excluded from the comparison. Among the three tested algorithms, the PL yielded the lowest and the PGS yielded the highest error rates (table 1). The high error rate of the PGS is perhaps due to the fact that the coalescence model might not be suitable for the heterogeneous genotype data consisting of both Caucasian and African American subjects.

Analysis When Missing Data Are Present

In order to assess the accuracy of the PL algorithm in the presence of missing data, we simulated 100 datasets. Each dataset is almost identical to the genotype data of the 11 individuals from the ACE dataset, except that for every marker of every individual, there is a 1% or 2% probability, respectively, to have missing values. Among all the markers with missing values, 50% miss two alleles, and the 50% miss one allele. The average number of incorrectly phased individuals was 3.2 in the 1% missing marker case and was 4.0 in the 2% case, in comparison to 2.1, 4.0, 3.0 for the PL, PGS, Clark's algorithms, respectively, when there was no missing data. The results suggested that the PL algorithm performs stably in the presence of missing data, but extra caution should be exercised. Markers with non-random patterns of typing failures should be re-designed or should be dropped from the genotyping set.

Kernel Mixture Model on the Haplotype Space

It may also be important to define a haplotype space which describes a relationship among the haplotypes. That is, when a haplotype h is present in the population, it is more likely for a haplotype that is "closer" to h, in the evolution sense, to be also present in the population. In other words, without further information, a new haplotype that is closer to someone already in the population is a better candidate. This idea can be helpful when too many distinct but closely related haplotypes are implied by the observed genotypes. However, the PGS is not derived from a consistent joint probability distribution, which makes many analyses difficult. To both incorporate the insight behind PGS and overcome their shortcomings, we directly model the distribution on the haplotype space which allows a certain smoothness among "nearby" haplotypes. This formulation uses the concept of smoothing most commonly used in the (continuous space)density estimation. In those problems, the "continuity" property of the unknown density function is facilitated by the continuity of the sample space (i.e., a distance is defined between any two points in the space).

Consider the haplotype with L linked marker loci. Since each marker has two possible alleles, the haplotype space is equivalent to the vertices space of a L-dimensional cube $Z_2^L$, which in the current context will be used to denote the haplotype space. For simplicity, we let elements in the space be denoted by c. As pointed out in Stephens (2001) and other studies related to evolution and coalescence processes, the closeness of two points $c_1$ and $c_2$ in $Z_2^L$ can be measured the number of mutations it needs to get from $c_1$ to $c_2$ or, more simply, the number of differing markers. Thus, a natural distance between $c_1$ and $c_2$ is the usual Euclidean distance $\|c_1-c_2\|$, which is also equal to the number of differing markers between $c_1$ and $c_2$. We can define a geometric decaying distribution $f_0(c;\mu)$ on $c \in Z_2^L$ as follows:

$$f_0(c;\mu) \propto \mu^{\|c\|}, \|c\| \leq \kappa$$

where $\|c\|$ is the distance from c to 0 (i.e., the number of 1's in c) and $\mu$ is related to the mutation rate. Thus, this distribution centers at the origin 0, and gives equal weights to the vertices that are equally distant from 0. The normalizing constant for this distribution is $$C = 1 + \mu L + \mu^2 \frac{L(L-1)}{2} + \ldots + \mu^\kappa \binom{L}{\kappa}$$

For practical purposes, we typically do not choose $\kappa > 3$. This distribution plays the role of a "kernel" in the density estimation literature and ~1 can either be controlled by the user to achieve certain "smoothness" for the estimated distribution or be estimated from mutation data. For any $h \in Z_2^L$, we can define $$f_h(c;\mu) = f_0(c+h;\mu)$$

which can be used to center the distribution at any haplotype h. Here we use the coordinate addition in modular of 2 (so that a+b=a−b).

With the kernel distribution in place, we can place a probability measure on the space of all population haplotype distributions P(c). More precisely, we assume that $$P(c) = \sum_{h \in Z_2^L} \theta_h f_h(c;\mu)$$

and $\theta = (\theta_h, h \in Z_2^L)$ follows a Dirichlet distribution with coefficient vector a. One can view this as a Dirichlet mixture of kernel distributions. This formulation allows one to capture certain relationship among the haplotypes and may be applicable in the general nonparametric Bayes analysis when certain smoothness of the underlying distribution is required.

To simplify the formulation, we can introduce a decoupling variable, the "hidden haplotype" h, for each haplotype c in the population. Both h and c are treated as missing data. The full model including the observed data can be stated as follows: Y is produced by randomly pairing 2n haplotypes Z drawn randomly from a haplotype population; the probability law for drawing haplotype c from the population can be characterized by a hierarchical process:

$$c|h \sim f_h(c;\mu)$$

$$h \sim \theta$$

$$\theta \sim \text{Dirichlet}(a).$$

Thus, the full model likelihood for the observed genotype data is $$P(Y|Z)P(Z|H,\mu)P(H|\theta)P(\theta),$$

where P(Y|Z) is 1 or 0 depending on whether Z is compatible with Y. Compared with a simple population model, this model put an extra layer of "hidden" haplotype between θ and the population haplotype Z. A Gibbs sampling algorithm consists of iterating the following conditional sampling steps:

$$Z|H, Y, \mu$$

$$H|Z, Y, \mu, \theta$$

$$\theta|H$$

The only uncharacterized step is the middle one. That is, for a single haplotype $z \in Z$, we want to sample its hidden variable h according to $$P(h) \propto f_h(z;\mu)\theta_h \quad (6)$$

We can further integrate out θ so that the sampling step (6) is replaced by $$P(h) \propto f_h(z;\mu)(n_h+a_h)$$

where $n_h$ is the counts of haplotype h in Z excluding the current one under consideration and $a_h$ is the pseudo-count used in the Dirichlet prior. The method outlined here can also be extended to the general nonparametric Bayes analyses in the case when one wants to infer a "smooth" distribution function.

Cystic Fibrosis Transmembrane Conductance Regulator (CFTR) Gene Dataset

Figure 3:
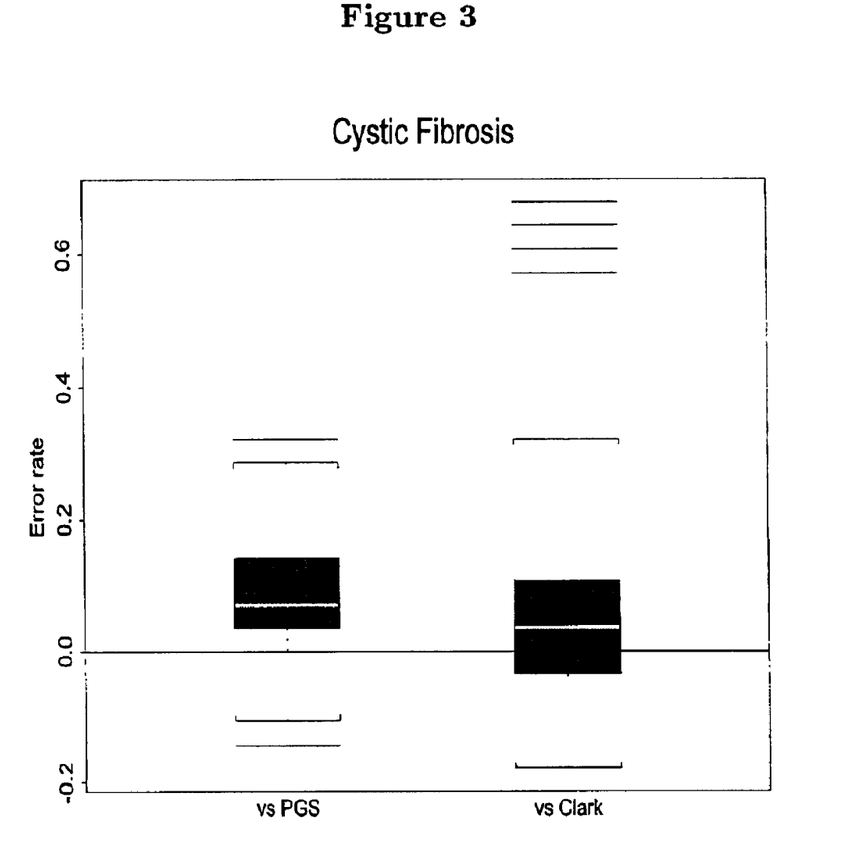
FIG. 3. Box-plots of $E_A$-$E_{PL}$, where $E_A$ and $E_{PL}$ denote the numbers of erroneous phase calls made by algorithm A (PGS or Clark's) and the PL algorithm, respectively, in each dataset. The higher the value the worse the algorithm A compared with the PL algorithm. One hundred datasets were simulated, where each consists of 28 hypothetical individuals with their genotypes generated by randomly permuting 56 of the 57 complete haplotypes of the 23 linked SNPs near the cystic fibrosis transmembrane conductance regulator gene provided by Kerem et al. (1989).

Cystic Fibrosis (CF) is one of the most common autosomal recessive disorders affecting whites, with an incidence of 1 case per 2,000 births. A 3-bp deletion in the open reading frame (Δ508) has been identified within the CFTR gene on chromosome 7q31, which constitutes over 60% of all chromosomes in affected individuals. Kerem et al. (1989) collected data on 23 SNPs in a 1.8-Mb candidate region on chromosome 7q31 from affected cases and healthy controls and this dataset has been analyzed by many haplotype-based LD methods [see Liu et al. (2001) for more references]. We took the subset of 57 haplotypes with no missing data from the 94 experimentally identified disease haplotypes in Kerem et al. (1989). These haplotypes were randomly permuted 100 times to form 100 datasets of 28 hypothetical individuals. The PL, PGS, and Clark's algorithms were applied to each of the datasets. The average error rates for the three algorithms are shown in Table 1. The PL algorithm produced a significantly lower error rate than the other two, although all mean error rates were greater than 30%. To illustrate how each algorithm performed in each simulated dataset, FIG. 3 also present a box-plot for the error differences between the PL and other algorithms. A reason for the poor performances of the three algorithms is presumably the excessive number (29) of distinct haplotypes in a small population (only 28 individuals).

5Q31 Region Dataset and Recombination Hotspot

A subset of the haplotype data from Daly et al. (2001) at 5q31 region data were used in our simulations to mimic the presence of recombination hotspots in the region. Between block 3 (with 9 component loci) and block 4 (with 11 component loci) shown in FIG. 2 of Daly et al. (2001), there is a recombination hotspot with an estimated haplotype exchange rate of 33%. By using the site of the hotspot as the reference point, we generated new haplotypes with 20 loci by picking the left segment (i.e. block 3) and the right segment (i.e. block 4) independently with the frequencies reported in Daly et al. (2001). For convenience, we discarded rare haplotypes of these two blocks and normalized their respectively common haplotype frequencies to 1. For each trial, we generated 40 haplotypes this way and formed 20 individuals. We are interested in seeing whether the PL method can perform better using the partition intentionally directed at the hotspot than that using the regular (default) partition. Among the 1,000 repeated simulations, the hotspot-cut (9|11-partition) outperformed the regular partition (10|10-partition) in 199 cases; the regular partition performed better in 42 cases; and the two methods produced identical results in the remaining 759 cases. The total number of incorrect predictions was reduced by 5% using the hot-spot cut. This shows that the PL method is insensitive to the presence of hotspots as long as they do not produce too many candidate partial haplotypes. In other words, the regular partition procedure can only lose accuracy if some "good" partial haplotypes are discarded prematurely due to an overwhelmingly large number of possibilities.

Population Theory-based Simulations

Simulation of the Bottleneck Effect

Figure 4:
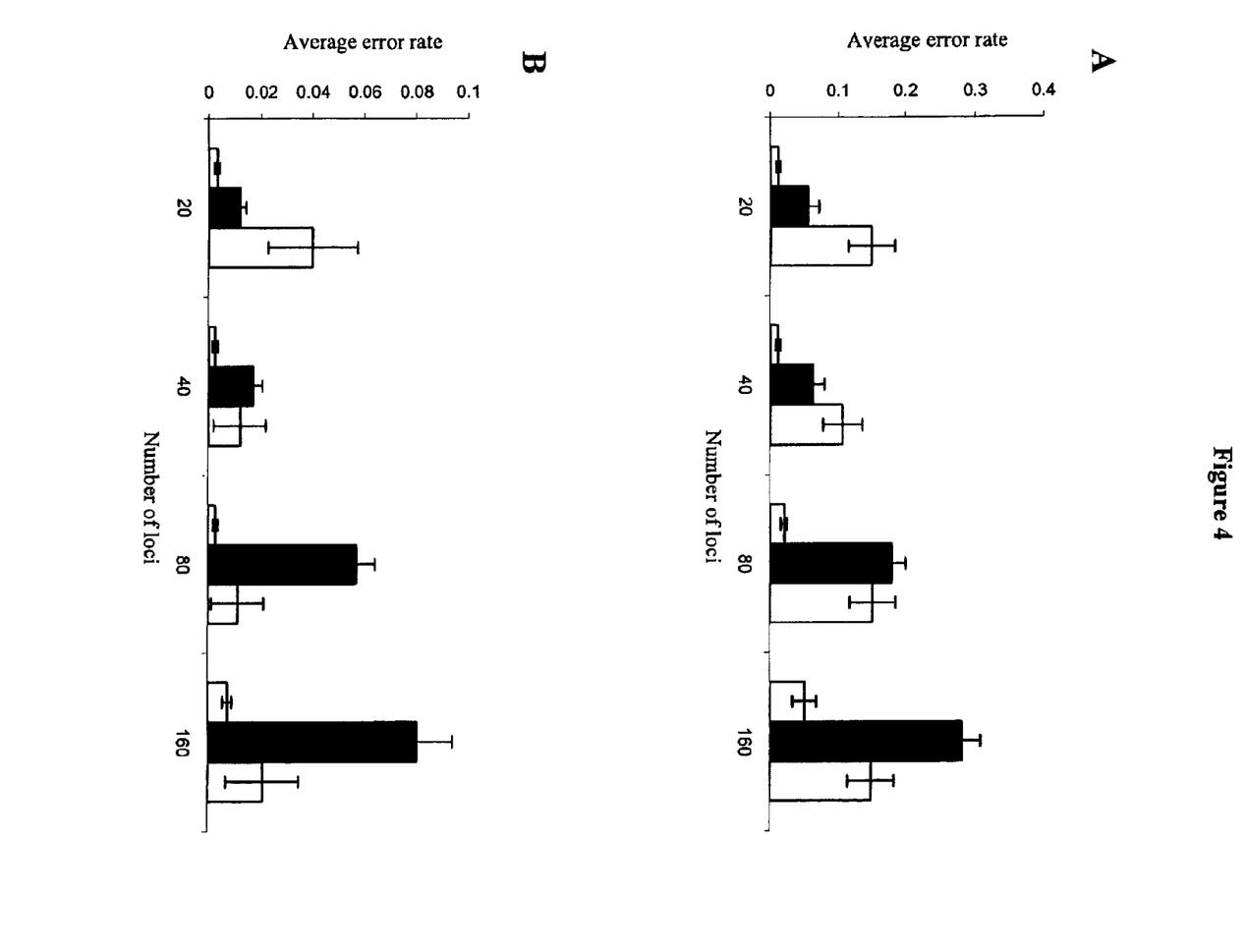
FIG. 4. Histograms of the average error rates (the number of erroneous phase calls divided by the total number of phase calls) for the simulations based on the "bottle-neck" model. We generated 100 independent datasets, each consisting of n pairs of unphased chromosomes with L linked SNPs. The chromosomes in each dataset are drawn randomly from a simulated population of the 102nd generation descendants of a founder group of 30 ancestors (with the mutation rate 10–5 and the cross-over rate 10–3 per generation). The growth rate for the first 2 generations was 2.0 and for the remaining generations 1.05. The error bars are shown as ±1 standard error. For L=20, 40, 80, 160, and (A) n=20, and (B) n=40, respectively, the error rates of the PL algorithm (open bars), the PGS algorithm (shaded bars), and the Clark's algorithm (dotted bars).

In this scheme, we simulated genotype datasets to mimic the "bottle-neck" phenomena (Reich et al. 2001). In the simulation, the population was evolved from 30 common ancestors about 1,000 years ago. During evolution, each individual's two haplotypes were randomly selected from its parental haplotype population, allowing for the occurrences of recombination and mutational events (see the caption of FIG. 4). The parameters used in our model were set to be comparable to the history of the European population (Liu et al. 2001). As shown in FIG. 4, the PL algorithm performed the best across various numbers of loci. The results obtained based on Clark's algorithm exhibited substantial variations in performance, whereas the PGS algorithm showed the highest average error rates when the total number of loci is large (e.g., L=80, 160).

Simulation Based on Coalescence-Model

Figure 5:
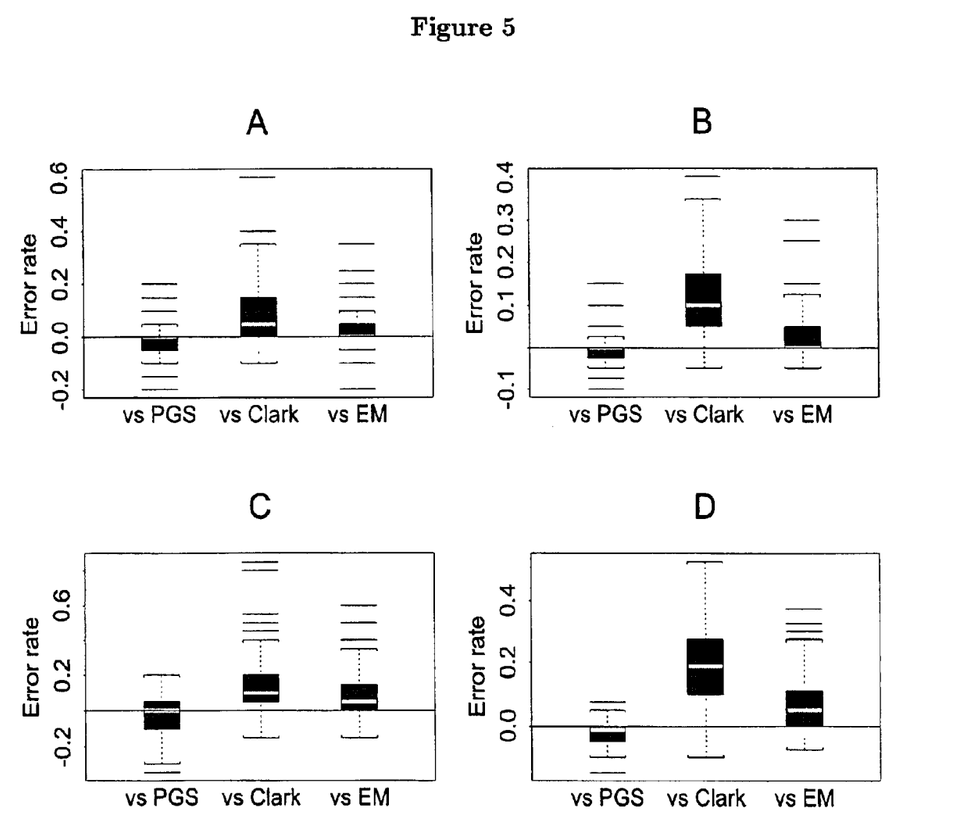
FIG. 5. Box-plots of $E_A$-$E_{PL}$, where $E_A$ and $E_{PL}$ refer to the numbers of erroneous phase calls made by algorithm A (PGS, Clark's, or EM) and the PL algorithm, respectively, for each simulated dataset. All the simulated datasets were based on coalescence model, and were obtained from the Simulation Gametes program of the Long lab (University of California, Irvine). A total of 100 replicates were carried out for a regional size of 10 units of 4Nc, each consisting of n pairs of unphased chromosomes with L linked SNP loci. (A) L=8, n=20; (B) L=8, n=40; (C) L=16, n=20; and (D) L=16, n=40.

In this scheme, samples of gametes were generated according to a neutral mutation drift model with recombination (Hudson 1991). For each simulated set of data, the number of gametes, the number of polymorphic sites, and the size of the region being considered in units of 4Nc were explicitly specified (see the caption of FIG. 5), and a total of 100 replications were made for each parameter setting. Because the data were generated according to the coalescence model upon which the iterative update formula of the PGS is based, the PGS of Stephens et al. (2001a) performed the best among the four algorithms tested. The PL algorithm was a close second (FIG. 5).

Discussion

Mapping genes that contribute to complex diseases such as breast cancer, diabetes, osteoporosis, and hypertension, will be a major challenge during the post-genome era (Risch 2000). In comparison testing SNPs one at a time, the "haplotype-centric" approach is advantageous for detecting susceptible genes, especially when allelic heterogeneity is present (Pritchard 2001, Daly et al. 2001). Determining haplotypes for a large number of linked SNPs using experimental methods can be very expensive, and infeasible. With the growing speed and efficiency in SNP identification and profiling, computational methods are perhaps the only practical means for large-scale haplotype determinations and they will continue to play an essential role in mapping complex traits.

Despite its simplicity and its dependence on the order of the individuals in the dataset, Clark's parsimony algorithm is intuitively appealing and effective when the dataset contains a sufficient number of homozygous individuals. The EM algorithm has been shown accurate in inferring common haplotypes (Tishkoff et al. 2000, Zhang et al. 2001). The PGS updates each person's haplotype pair $z_i$ by drawing from $P_i(z_i|y_i, Z_{[-i]})$, a distribution crafted based on the coalescence theory. As mentioned in Stephens et al. (2001a), the $P_i$ do not correspond to the conditionals of a proper joint distribution (which is why the method is named the "pseudo-Gibbs sampler"). Therefore, although the induced Markov chain in PGS is still geometric convergent, its stationary distribution may depend on the order of the $y_i$ (Gehnan and Speed 1993), and the pseudo-posterior probabilities attached to the constructed haplotypes become difficult to interpret. Although the PGS provide a guide for each locus in the haplotype whether this position is difficult to infer, it, at least in some implementations, lacks a measure of the overall goodness of the constructed haplotypes, making it difficult to compare outputs generated from multiple runs. Nevertheless, the PGS provides an appealing strategy for incorporating evolution effects in haplotype construction. Our simulations showed that the PGS is advantageous when the population conforms to the coalescence assumption.

The Bayesian Monte Carlo method provided by this description utilizes two computational techniques were utilized in our algorithm: prior annealing and PL. Prior annealing helps the algorithm escape from a local maxima. PL helps construct the whole haplotype by recursively stacking up haplotype segments. This "block-by-block" strategy not only allows for the handling of a large number of SNPs, but also deals with the local-mode problem better than the "piece-by-piece" strategy of the PGS. The resulting PL algorithm was compared with the PGS, the EM, and Clark's algorithms using both real data and the ones simulated under different scenarios. Overall, the PL algorithm is robust; it outperformed at least some other algorithms in all real data applications and was second to the PGS algorithm only under the coalescence-based simulation. The PL algorithm also performed in the presence of a small percentage of missing marker data.

The PL algorithm, similar to the EM algorithms, assumes the HWE and random mating, which is appropriate for populations of large sizes that have existed for a long period of time. Both Stephens et al. (2001a) and Fallin and Schork (2001) performed assessments of their algorithms when the HWE is violated and concluded that the impact on their algorithms were not dramatic. We compared the performances of the PL, PGS, Clark's, and EM algorithms under five different levels of HWE violations and found that the PL and the EM exhibited strong algorithmic stability.

In a study of the effect of population mixture (another way of violating the HWE), we simulated 100 datasets, each consisting of three independent subgroups of 10 individuals generated from a coalescence model under the HWE. The PL algorithm performed marginally better than the PGS despite the fact that the PGS is rooted for the coalescence model.

Our simulations based on the 5q31 data suggested that the partition step was not sensitive to the presence of recombination hotspot, although knowing and partitioning at the hotspot can bring in marginal improvement. Daly et al. (2001) showed that, despite the presence of local hotspots, there is still clear long-range LD among blocks, suggesting that the majority of the recombination hotspots are moderate. Indeed, Farrall et al. (1999) reported that the ACE 52-locus haplotype analyzed in the Result section has a recombination hotspot located between the $9^{th}$ and the $12^{th}$ loci. The partition sites of the PL algorithm in the vicinity of this recombination hotspot, however, follow immediately after marker loci 6 and 13. As shown by our results, the accuracy of the PL algorithm was not compromised. Since the recombination hotspots are generally not known in advance, it is of interest to develop an automated procedure to screen for "stable" blocks of low haplotype diversity and conduct PL simultaneously.

The PL algorithm was implemented in ANSI C++ and compiled on the Red Hat Linux OS using Dell PowerEdge 4400 Server with twin 866 MHz Pentium Xeon processors. The PL algorithm runs about three times faster than the PGS (implemented as PHASE with a moderate number of iterations). In our simulation studies of the bottleneck effect, for L=20, 40, 80, 160 loci, and for n=20, the CPU time was approximately 2.3, 6.1, 11.6, and 25.9 seconds, respectively; for n=40, approximately 3.8, 9.2, 18.9, and 36.5 seconds, respectively. It is noted that the data complexity for the same number of SNPs can still vary tremendously since the amount of LD present across the genomic region can vary dramatically. For a sample of 100 individuals, our software currently can handle 256 SNPs; for a sample of 1,000 individuals, the software can handle 50 SNPs. Our software outputs not only the putative haplotypes, but also measures of their accuracies as well as the overall likelihood. The user can conduct multiple runs and select the result with the highest likelihood.

Once haplotypes are constructed, various statistical methods can be applied to detect haplotype-disease associations and to cluster/classify patients. These include chi-square test, likelihood ratio test (Fallin et al. 2001), logistic regression (Wallenstein et al. 1998), cladistic analysis (Templeton 1995; Heng and Low 2000), and haplotype pattern mining method (Toivonen et al. 2000). We believe that, by coupling with some haplotype-based LD analysis, the utility of our method may have significant implications in positional cloning for complex traits.

Other

Dirichlet Distribution: We say that a random vector X= $(X_1, \ldots, X_n)$ follows the Dirichlet distribution Dir $(\alpha_1, \ldots, \alpha_n)$ if its density is of the form $$f(x_1, \ldots, x_n) = \frac{\Gamma(\alpha_1 + \ldots + \alpha_n)}{\Gamma(\alpha_1) \times \ldots \times \Gamma(\alpha_n)} x_1^{\alpha_1 - 1} \times \ldots \times x_n^{\alpha_n - 1},$$

where $\Sigma x_i = 1$, $x_i \geq 0$, and $\Gamma(a)$ is the Gamma function. Thus, it is necessary that $X_i \geq 0$ and $X_1 + \ldots + X_n = 1$, implying that it is a random probability vector. A simple property of this distribution is that $EX_i = \alpha_i / \Sigma \alpha_j$.

HAPLOTYPER: This program implements the partition-ligation Gibbs sampling method described in this article.

EM-DeCODER: This program implements the EM-algorithm for haplotype constructions as described in this article. Its input and output file formats are the same as HAPLOTYPER.

HaplotypeManager: A simple user interface for displaying the haplotype data and visualizing the haplotype distributions has been implemented using JDK v.1.0.

Further description of an exemplary implementation of at least some methods described herein can be found in Niu et al. (2002) *Am. J. Hum. Genet.* 70:157–169.

The invention can be implemented in digital electronic circuitry, or in computer hardware, firmware, software, or in combinations thereof. Apparatus of the invention can be implemented in a computer program product tangibly embodied in a machine-readable storage device for execution by a programmable processor; and method actions can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including, by way of example, semiconductor memory devices, such as EPROM, EEPROM, and flash memory devices; magnetic disks such as, internal hard disks and removable disks; magneto-optical disks; and CD_ROM disks. Any of the foregoing can be supplemented by, or incorporated in, ASICs (application-specific integrated circuits).

Figure 6:
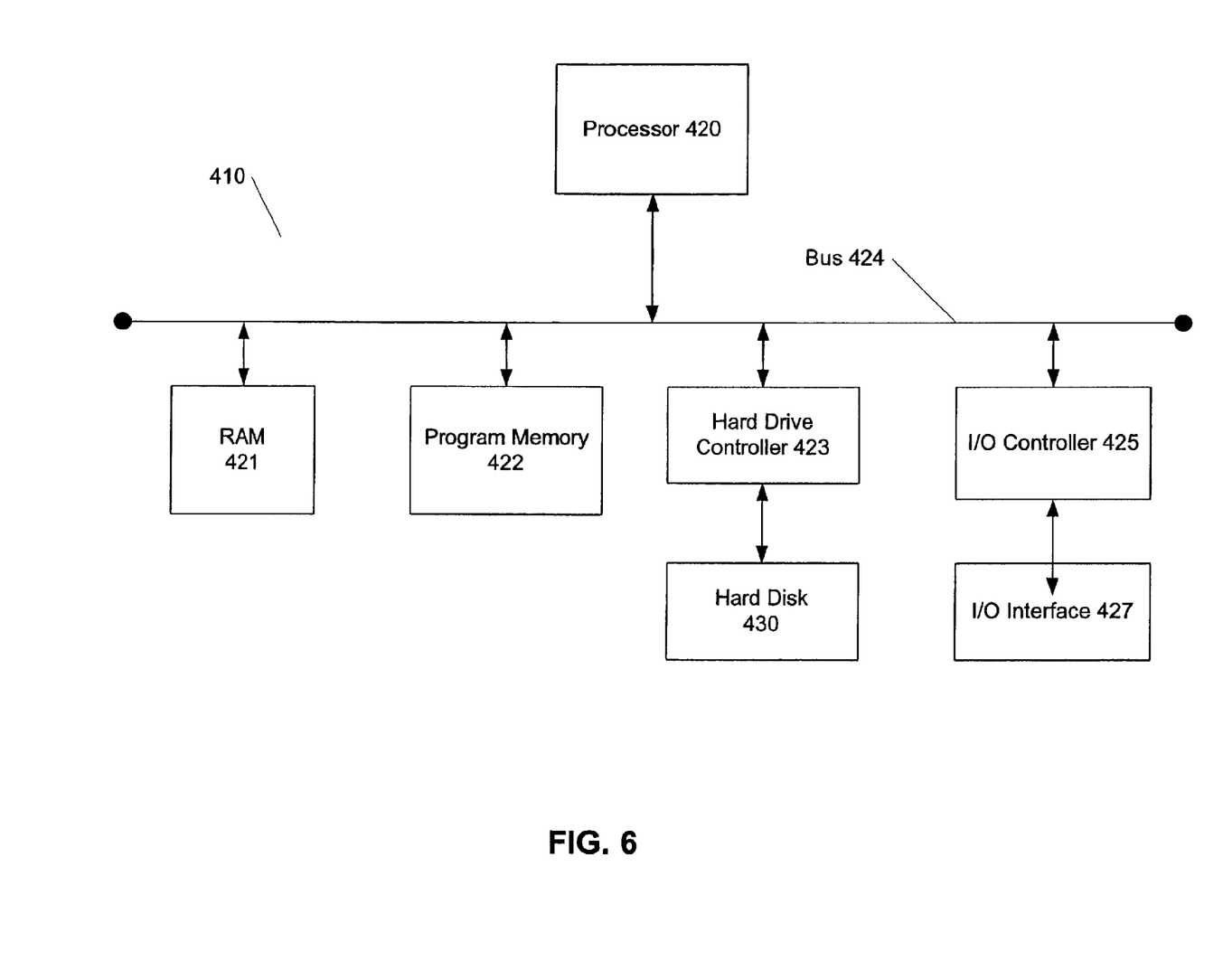
FIG. 6. is an exemplary computer system that can be used to implement aspects of the invention.

An example of one such type of computer is shown in FIG. 6, which shows a block diagram of a programmable processing system (system) 410 suitable for implementing or performing the apparatus or methods of the invention. The system 410 includes a processor 420, a random access memory (RAM) 421, a program memory 422 (for example, a writable read-only memory (ROM) such as a flash ROM), a hard drive controller 423, and an input/output (I/O) controller 424 coupled by a processor (CPU) bus 425. The system 410 can be preprogrammed, in ROM, for example, or it can be programmed (and reprogrammed) by loading a program from another source (for example, from a floppy disk, a CD-ROM, or another computer).

The hard drive controller 423 is coupled to a hard disk 430 suitable for storing executable computer programs, including programs embodying the present invention, and data including storage. The I/O controller 424 is coupled by means of an I/O bus 426 to an I/O interface 427. The I/O interface 427 receives and transmits data in analog or digital form over communication links such as a serial link, local area network, wireless link, and parallel link.

Non-limiting examples of execution environments include computers running Linux Red Hat OS, Windows XP (Microsoft) or better or Solaris 2.6 or better (Sun Microsystems) operating systems.

Other embodiments of the invention are within the appended claims.

REFERENCES

Akey J, Jin L, Xiong M (2001) Haplotypes vs single marker linkage disequilibrium tests: what do we gain? Eur J Hum Genet 9:291–300.

Beaudet L, Bedard J, Breton B, Mercuri R J, Budarf M L (2001) Homogeneous assays for single-nucleotide polymorphism typing using AlphaScreen. Genome Res 11:600–608.

Bradshaw M S, Bollekens J A, Ruddle F H (1995) A new vector for recombination-based cloning of large DNA fragments from yeast artificial chromosomes. Nucleic Acids Res 23:4850–4856.

Chen R, Liu J S (1996) Predictive updating methods with application to Bayesian classification. J Roy Stat Soc Series B 58:397–415.

Chiano M N, Clayton D G (1998) Fine genetic mapping using haplotype analysis and the missing data problem. Ann Hum Genet 62 (Pt 1):55–60.

Clark A G (1990) Inference of haplotypes from PCR-amplified samples of diploid populations. Mol Biol Evol 7:111–122.

Cox D, Boillot C, Canzian F (2001) Data mining: Efficiency of using sequence databases for polymorphism discovery. Hum Mutat 17:141–150.

Daly M J, Rioux J D, Schaffner S F, Hudson T J, Lander E S (2001) High-resolution haplotype structure in the human genome. Nat Genet 29:229–232.

Dempster A P, Laird N M, Rubin D B (1977) Maximum likelihood from incomplete data via EM algorithm. J Roy Stat Soc Series B 39:1–38.

Douglas J A, Boehnke M, Gillanders E, Trent J M, Gruber S B (2001) Experimentally-derived haplotypes substantially increase the efficiency of linkage disequilibrium studies. Nat Genet 28:361–364.

Drysdale C M, McGraw D W, Stack C B, Stephens J C, Judson R S, Nandabalan K, Arnold K, Ruano G, Liggett S B (2000) Complex promoter and coding region beta 2-adrenergic receptor haplotypes alter receptor expression and predict in vivo responsiveness. Proc Natl Acad Sci USA 97:10483–10488.

Excoffier L, Slatkin M (1995) Maximum-likelihood estimation of molecular haplotype frequencies in a diploid population. Mol Biol Evol 12:921–927.

Fallin D, Cohen A, Essioux L, Chumakov I, Blumenfeld M, Cohen D, Schork N J (2001) Genetic Analysis of Case/Control Data Using Estimated Haplotype Frequencies: Application to APOE Locus Variation and Alzheimer's Disease. Genome Res 11:143–151.

Fallin D, Schork N J (2000) Accuracy of haplotype frequency estimation for biallelic loci, via the expectation-maximization algorithm for unphased diploid genotype data. Am J Hum Genet 67:947–959.

Fan J B, Chen X, Halushka M K, Bemo A, Huang X, Ryder T, Lipshutz R J, Lockhart D J, Chakravarti A (2000) Parallel genotyping of human SNPs using generic high-density oligonucleotide tag arrays. Genome Res 10:853–860.

Farrall M, Keavney B, McKenzie C, Delepine M, Matsuda F, Lathrop G M (1999) Fine-mapping of an ancestral recombination breakpoint in DCP 1. Nat Genet 23:270–271.

Gelman A, Speed T P (1993) Characterizing a joint probability distribution by conditionals, J Roy Stat Soc Ser B 55:185–188.

Hacia J G, Fan J B, Ryder O, Jin L, Edgemon K, Ghandour G, Mayer R A, Sun B, Hsie L, Robbins C M, Brody L C, Wang D, Lander E S, Lipshutz R, Fodor S P, Collins F S (1999) Determination of ancestral alleles for human single-nucleotide polymorphisms using high-density oligonucleotide arrays. Nat Genet 22:164–167.

Hawley M E, Kidd K K (1995) HAPLO: a program using the EM algorithm to estimate the frequencies of multi-site haplotypes. J Hered 86:409–411.

Heng C K, Low P S (2000) Cladistic analysis: its applications in association studies of complex diseases. Ann Acad Med Singapore 29:313–321.

Hodge S E, Boehnke M, Spence M A (1999) Loss of information due to ambiguous haplotyping of SNPs. Nat Genet 21:360–361.

Hudson R R (1991) Gene genealogies and the coalescent process. In: Futuyma D, Antonovics J (eds) Oxford surveys in evolutionary biology, vol 7. Oxford University Press, Oxford, pp 1–44.

Israel E, Drazen J M, Liggett S B, Boushey H A, Chemiack R M, Chinchilli V M, Cooper D M, Fahy J V, Fish J E, Ford J G, Kraft M, Kunselman S, Lazarus S C, Lemanske R F, Martin R J, McLean D E, Peters S P, Silverman E K, Sorkness C A, Szefler S J, Weiss S T, Yandava C N (2000) The effect of polymorphisms of the beta(2)-adrenergic receptor on the response to regular use of albuterol in asthma. Am J Respir Crit Care Med 162:75–80.

Judson R, Stephens J C (2001) Notes from the SNP vs. haplotype front. Pharmacogenomics 2:7–10.

Kerem B, Rommens J M, Buchanan J A, Markiewicz D, Cox T K, Chakravarti A, Buchwald M, et al (1989) Identification of the cystic fibrosis gene: genetic analysis. Science 245:1073–1080.

Lander E S, Botstein D (1987) Homozygosity mapping: a way to map human recessive traits with the DNA of inbred children. Science 236:1567–1570.

Lawrence C E, Altschul S F, Boguski M S, Liu J S, Neuwald A F, Wootton J C (1993) Detecting subtle sequence signals: a Gibbs sampling strategy for multiple alignment. Science 262:208–214.

Liu J S (1994) The collapsed Gibbs sampler Bayesian computation with applications to a gene regulation problem. J Am Stat Assoc 89:958–966.

Liu J S (2001) *Monte Carlo Strategies in Scientific Computing*. Springer-Verlag, New York.

Liu J S, Sabatti C, Teng J, Keats B J, Risch N (2001) Bayesian analysis of haplotypes for linkage disequilibrium mapping. Genome Res 11: 1716–1724.

Lizardi P M, Huang X, Zhu Z, Bray-Ward P, Thomas D C, Ward D C (1998) Mutation detection and single-molecule counting using isothermal rolling-circle amplification. Nat Genet 19:225–232.

Long J C, Williams R C, Urbanek M (1995) An E-M algorithm and testing strategy for multiple-locus haplotypes. Am J Hum Genet 56:799–810.

Martinez F D, Graves P E, Baldini M, Solomon S, Erickson R (1997) Association between genetic polymorphisms of the beta2-adrenoceptor and response to albuterol in children with and without a history of wheezing. J Clin Invest 100:3184–3188.

Michalatos-Beloin S, Tishkoff S A, Bentley K L, Kidd K K, Ruano G (1996) Molecular haplotyping of genetic markers 10 kb apart by allele-specific long-range PCR. Nucleic Acids Res 24:4841–4843.

Niu T, Seielstad M, Zeng X, Apffel A, Li G, Hahnenberger K, Xu X (2001a) Detection of novel ALAD gene polymorphisms using denaturing high-performance liquid chromatography. Hum Biol 73:429–442.

Niu T, Chen X, Xu X (2001b) Angiotensin converting enzyme gene polymorphism and cardiovascular disease: Therapeutic Implications. Drugs (in press). Pritchard J K (2001) Are rare variants responsible for susceptibility to complex diseases? Am J Hum Genet 69:124–137.

Ranade K, Chang M S, Ting C T, Pei D, Hsiao C F, Olivier M, Pesich R, Hebert J, Chen Y D, Dzau V J, Curb D, Olshen R, Risch N, Cox D R, Botstein D (2001) High-throughput genotyping with single nucleotide polymorphisms. Genome Res 11:1262–1268.

Reich D E, Cargill M, Bolk S, Ireland J, Sabeti P C, Richter D J, Lavery T, Kouyoumjian R, Farhadian S F, Ward R, Lander E S (2001) Linkage disequilibrium in the human genome. Nature 411:199–204.

Reihsaus E, Innis M, MacIntyre N, Liggett S B (1993) Mutations in the gene encoding for the beta 2-adrenergic receptor in normal and asthmatic subjects. Am J Respir Cell Mol Biol. 8:334–339.

Rieder M J, Taylor S L, Clark A G, Nickerson D A (1999) Sequence variation in the human angiotensin converting enzyme. Nat Genet 22:59–62.

Risch N J (2000) Searching for genetic determinants in the new millennium. Nature 405:847–856.

Ross P, Hall L, Smirnov I, Haff L (1998) High-level multiplex genotyping by MALDI-TOF mass spectrometry. Nat Biotechnol 16:1347–1351.

Ruano G, Kidd K K, Stephens J C (1990) Haplotype of multiple polymorphisms resolved by enzymatic amplification of single DNA molecules. Proc Natl Acad Sci USA 87:6296–6300.

Schroeder S A, Gaughan D M, Swift M (1995) Protection against bronchial asthma by CFTR delta F508 mutation: a heterozygote advantage in cystic fibrosis. Nat Med 1:703–705.

Stephens M, Smith N J, Donnelly P (2001a) A new statistical method for haplotype reconstruction from population data. Am J Hum Genet 68:978–989.

Stephens J C, Schneider J A, Tanguay D A, Choi J, Acharya T, Stanley S E, Jiang R, et al (2001b) Haplotype variation and linkage disequilibrium in 313 human genes. Science 293:489–493.

Templeton A R (1995) A cladistic analysis of phenotypic associations with haplotypes inferred from restriction endonuclease mapping or DNA sequencing. V. Analysis of case/control sampling designs: Alzheimer's disease and the apoprotein E locus. Genetics 140:403–409.

Tishkoff S A, Pakstis A J, Ruano G, Kidd K K (2000) The accuracy of statistical methods for estimation of haplotype frequencies: an example from the CD4 locus. Am J Hum Genet 67:518–522.

Toivonen H T, Onkamo P, Vasko K, Ollikainen V, Sevon P, Mannila H, Herr M, Kere J (2000) Data mining applied to linkage disequilibrium mapping. Am J Hum Genet 67:133–145.

Tyagi S, Kramer F R (1996) Molecular beacons: probes that fluoresce upon hybridization. Nat Biotechnol. 14:303–308.

Wallenstein S, Hodge S E, Weston A (1998) Logistic regression model for analyzing extended haplotype data. Genet Epidemiol 15:173–181.

Woolley A T, Guillemette C, Li Cheung C, Housman D E, Lieber C M (2000) Direct haplotyping of kilobase-size DNA using carbon nanotube probes. Nat Biotechnol 18:760–763.

Zhang S, Pakstis A J, Kidd K K, Zhao H (2001) Comparisons of two methods for haplotype reconstruction and haplotype frequency estimation from population data. Am J Hum Genet 69:906–914.

Zhao H, Zhang S, Merikangas K R, Trixler M, Wildenauer D B, Sun F, Kidd K K (2000) Transmission/disequilibrium tests using multiple tightly linked markers. Am J Hum Genet 67:936–946.

TABLE 1

Comparison of the average error rates (defined as the number of erroneous phase calls divided by the total number of phase calls) of the partition-ligation (PL) algorithm, the pseudo-Gibbs sampling (PGS) algorithm, and Clark's algorithm for the two real datasets on (1) the angiotensin I converting enzyme (ACE) gene, and (2) the cystic fibrosis transmembrane conductance regulator (CFTR gene. For the ACE gene, the average error rates were obtained by 100 independent runs of each algorithm. For the CFTR gene, the average error rates were for 100 datasets generated by randomly permuting 56 of the 57 complete haplotypes reported in Kerem et al. (1989).

| Algorithm* | ACE (52 loci) | | CFTR (23 loci) | |
|---|---|---|---|---|
| | Average Error Rate | S.E. | Average Error Rate | S.E. |
| PL | 0.19 | 0.003 | 0.39 | 0.008 |
| PGS | 0.36 | 0.004 | 0.48 | 0.009 |
| Clark | 0.27 | 0.000 | 0.47 | 0.018 |

*The EM algorithm was excluded from the comparison because it cannot handle more than 15 heterozygous loci in the data.

What is claimed:

1. A method comprising:
    separating a dataset that includes genotypic information for a plurality of markers for each of a plurality of individuals into subdatasets, each subdataset including the genotypic information for a subset of the plurality of markers;
    for each subdataset, identifying haplotypes compatible with marker information for each marker of the subset and for each individual of the plurality; and
    for each individual, assembling the haplotypes from each of the subsets to provide the individual's haplotype with respect to the plurality of markers.

2. The method of claim 1 wherein the separating and/or assembling is effected recursively.

3. The method of claim 1 wherein the dataset is separated into a number of subsets, the number being a power of two ($2^x$).

4. The method of claim 1 wherein the identifying comprises maximizing the likelihood of haplotype frequencies in a population.

5. The method of claim 1 wherein the identifying comprises the Gibbs sampling methods or the Expectation-Maximization (EM) algorithm.

6. The method of claim 5 wherein the identifying comprises a Markov chain Monte Carlo algorithm.

7. The method of claim 5 wherein the identifying comprises a parsimony method.

8. The method of claim 1 wherein the identifying comprises assigning pseudocounts corresponding to a plurality of possible haplotypes and iteratively reducing the pseudocounts.

9. The method of claim 1 further comprising outputting a result based on the haplotype of at least one individual of the plurality.

10. The method of claim 1 wherein at least some of the subsets are overlapping.

11. The method of claim 1 wherein at least one of the subsets is interleaved with another subset.

12. The method of claim 1 wherein the dataset includes missing or ambiguous marker information and an allele is assigned to the missing or ambiguous marker.

13. The method of claim 1 wherein the dataset includes marker information for at least ten markers.

14. The method of claim 1 wherein the markers comprise biallelic SNPs.

15. A method comprising:

sending, to a computer unit, unphased genotypic information about a plurality of gene markers for a plurality of individuals; and receiving, from the computer unit, phased genotypic information about the plurality of gene markers for the individual, wherein the computer unit determined the phased genotypic information using a method according to claim 1.

16. The method of claim 1 wherein the individuals are human individuals.

17. An article of machine readable medium, having encoded thereon instructions causing a processor to effect a method comprising:

separating a dataset that includes genotypic information for a plurality of markers for each of a plurality of individuals into subdatasets, each subdataset including the genotypic information for a subset of the plurality of markers;

for each subdataset, identifying haplotypes compatible with marker information for each marker of the subset and for each individual of the plurality; and for each individual, assembling the haplotypes from each of the subsets to provide the individual's haplotype with respect to the plurality of markers.

18. The article of claim 17 wherein the separating and/or assembling is effected recursively.

19. The article of claim 17 wherein the dataset is separated into a number of subsets, the number being a power of two ($2^x$).

20. The article of claim 17 wherein the identifying comprises maximizing the likelihood of haplotype frequencies in a population.

21. The article of claim 17 wherein the identifying comprises the Gibbs sampling methods or the Expectation-Maximization (EM) algorithm.

22. The article of claim 21 wherein the identifying comprises a Markov chain Monte Carlo algorithm.

23. The article of claim 21 wherein the identifying comprises a patsimony method.

24. The article of claim 17 wherein the identifying comprises assigning pseudocounts corresponding to a plurality of possible haplotypes and iteratively reducing the pseudocounts.

25. The article of claim 17 wherein at least one of the subsets are overlapping.

26. The article of claim 17 wherein at least one of the subsets is interleaved with another subset.

27. The article of claim 17 wherein the dataset includes missing ambiguous marker information and an allele is assigned to the missing or ambiguous marker.

* * * * *